(12) United States Patent
Leide et al.

(10) Patent No.: US 6,556,295 B2
(45) Date of Patent: Apr. 29, 2003

(54) DEVICE AND METHOD FOR OPTICAL MEASUREMENT

(75) Inventors: Erland Leide, Helsingborg (SE); Nils Wihlborg, Helsingborg (SE); Håkan Wedelsbäck, Ängelholm (SE); Tomas Jonasson, Helsingborg (SE); Roger Ylikangas, Rydebäck (SE)

(73) Assignee: Foss Tecator AB, Hoganas (SE)

( * ) Notice: Subject to any disclaimer, the term of this patent is extended or adjusted under 35 U.S.C. 154(b) by 248 days.

(21) Appl. No.: 09/770,233

(22) Filed: Jan. 29, 2001

(65) Prior Publication Data

US 2002/0060790 A1 May 23, 2002

(30) Foreign Application Priority Data

Nov. 17, 2000 (SE) .............................................. 0004534

(51) Int. Cl.⁷ .............................................. G01N 21/01
(52) U.S. Cl. .................................................... 356/244
(58) Field of Search ................................ 356/244, 335, 356/337, 338, 343

(56) References Cited

U.S. PATENT DOCUMENTS 4,376,609 A * 3/1983 Bohman et al. ............ 414/335
4,742,228 A * 5/1988 Bischoff .................... 250/341.1
5,818,045 A * 10/1998 Mark et al. ............. 250/339.12
6,115,115 A * 9/2000 Skarie et al. .................. 356/73

FOREIGN PATENT DOCUMENTS

| JP | 01-161136 | 6/1989 |
| JP | 09-292344 | 11/1997 |

* cited by examiner

Primary Examiner—Michael P. Stafira
(74) Attorney, Agent, or Firm—Browdy and Neimark

(57) ABSTRACT

A method and device for optical measuring of small particles for analysis of the quality of the particles. A sample-feeding carrier is adapted to take up particle samples in sample holders and transport the particle samples to a place for optical measurement. A mirror-supporting means follows the movement of the carrier and has mirrors matching the sample holders. A device illuminates a particle sample when positioned for optical measurement and a detector, which is sensitive to electromagnetic radiation, records a result of optical measurement of the illuminated particle sample. A mirror reflects the particle sample, so that a mirror image thereof stands essentially still seen from the detector, when a measurement is being recorded, owing to the fact that the mirror image of the particle sample falls on a center axis of the movement of the mirror-supporting means.

27 Claims, 3 Drawing Sheets

DEVICE AND METHOD FOR OPTICAL MEASUREMENT

FIELD OF THE INVENTION

The invention relates to a method and a device for optical measuring of small particles, such as grains from cereals and like crops, for analysis of the quality of the particles.

BACKGROUND OF ART

Inspection of different kinds of cereals and other crops is today made all over the world to determine the quality of the cereals in commercial transactions and handling. The inspection aims at examining a selected representative sample from a large consignment and determining the presence of non-desirable grains and particles. The non-approved grains and particles are classified and the quantity of each class is determined. Owing to the distribution of the various grains, the sample and, thus, the consignment will be given a grading which is a decisive factor in connection with payment and handling of the consignment.

Today most cereal inspections are carried out entirely manually. A skilled inspector has often passed through a comprehensive education of many years. Nevertheless there are great deviations in the analyses/classifications between different inspectors owing to, among other things, personal assessments and varying conditions of lighting. Deviations also occur in each individual inspector because of, for example, the degree of fatigue.

It is therefore desirable for the methods of analysis to be automated to reduce the deviations and create a more stable situation with a more transparent grading process. For an exact grading of the sample, the grains must be separated from each other to allow each individual grain to be classified. This can be made either by physical separation or by means of digital image processing.

Thus, use is presently made of certain optical measuring methods for analysis of the quality of the grains. These measuring methods are based on a grain being illuminated, whereupon some sort of detection is made of the light emitted from the grain for analysis of the quality of the grain. The illumination may vary significantly regarding, for example, from which direction the grain is illuminated, which wavelength is used, etc. The detection may vary in respect of whether e.g. reflected light, transmitted light or diffuse light is detected.

Instruments using one or more of these optical measuring methods have some kind of physical sorting out of the grains so that only one grain at a time is measured. It should, however, not be necessary to interrupt the feeding of grains each time a grain is to be measured. This means that it must be possible to optically measure moving grains. This places great demands on the optical detection to prevent the movement of the grain from spoiling the measurement. An extremely quick detector must be used, which causes great costs, or the feeding of samples must be carried out so slowly that a less expensive, slower detector will manage, which results in a long time of waiting between measurements of two grains.

A quick detector also involves peripheral equipment, which requires a great deal of space. Since the time of exposure must be very short, the detector also requires that large amounts of light be available, and this requirement is difficult to satisfy.

To prevent movement blur from arising, a grain cannot move more than extremely marginally during the measuring time of the detector. The measuring time of the detector and the distance a grain can move during the measurement thus decide the speed at which the samples can be fed. For an ordinary detector, this means a very low speed and unacceptable analyzing times.

A compromise could be to vary the speed of the feeding, in such manner that the grains are fed quickly when no measurement occurs, and slowly during measurement. This, however, causes wear on mechanical components feeding the samples since acceleration and retardation occur constantly. This also places demands on the control so that the correct speed is kept up during and between measurements.

SUMMARY OF THE INVENTION

An object of the present invention is to provide a quick automatic method for optical measurement of particles for analysis. A further object is to solve the above problems and provide optical measurements of particles fed at a high speed, using conventional, relatively inexpensive detectors.

The objects of the invention are achieved by means of a device according to claim 1 and a method according to claim 14. Further advantages of the invention are evident from dependent claims 2–13 and 15–27.

Thus, the invention provides a device for optical measuring of small particles, such as grains from cereals and like crops, for analysis of the quality of the particles. The device comprises a sample-feeding carrier, which is adapted to take up particle samples, which each comprise at least one particle, in sample holders and transport the particle samples to a place for optical measurement, a mirror-supporting means, which follows the movement of the carrier and has a mirror for each sample holder, a device for illuminating a particle sample when this is positioned for optical measurement, and a detector which is sensitive to electromagnetic radiation for recording at least one result of an optical measurement of the illuminated particle sample. A mirror in the mirror-supporting means reflects the particle sample, so that a mirror image thereof stands essentially still seen from the detector, when the measurement is being recorded, owing to the fact that the mirror image of the particle sample falls on a center axis of the movement of the mirror-supporting means.

This design implies that the time of exposure can be extended significantly in the detector since the mirror image of the particle stands still. The extended time of exposure then causes no problems with movement blur and conventional detectors can be used. Particles can thus be fed at a high speed, which results in a high measuring speed. By the mirror image standing essentially still is meant that no translational movement occurs, but only a small degree of turning of the mirror image, owing to the movement of the mirror in front of the detector. This turning, however, is so small that no or very little movement blur arises.

According to a preferred embodiment, the sample-feeding carrier is adapted to feed the particle samples during continuous movement.

Since the particles can be fed at a high speed without causing movement blur in the detector, there is no need for a higher feeding speed between the measurements. The continuous movement means that the wear on mechanical components in the device is insignificant.

The detector is preferably an image-recording means, which records an image of the particle sample in the optical measurement. An image contains such an amount of information about the particle sample that it can be analyzed in respect of several properties on the basis of one measurement.

The device advantageously comprises a means for image analysis of the recorded image, an image of a particle sample, which comprises several particles, being divisible, with the aid of the means for image analysis, into images of one particle each. As a result, several particles can be analyzed on the basis of one image. The device will not be dependent on the condition that only one particle at a time is fed to the optical measurement.

The image-recording means conveniently is a digital camera. This means that an image of whole particles is recorded and image analysis can be used to analyze parts of the particles. No averaging as regards the light from the particle occurs, which could conceal defects or make the discovery of defects difficult. The digital camera produces an image in digital format, which is needed for the image analysis.

According to a preferred embodiment, the sample holders are adapted to take up only one particle. This means that a physical separation of the particles is obtained. In case of several analyses of the same particle using different illumination techniques, a physical separation is preferred.

The carrier is preferably circular and rotates to feed the particle samples. This ensures easy feeding of samples, and the feeding frequency can easily be made constant.

According to a further preferred embodiment, the mirror-supporting means and the carrier are interconnected by a central shaft and thus follow each other's movements. This means that exact following of the movements of the particle samples can easily be provided. Exact following is important for the mirror image to stand still on the center axis of the movement.

The mirrors in the mirror-supporting means are preferably arranged at an angle of 45° to the center axis, the distance between the particle sample and the associated mirror being the same as the distance between the mirror and the center axis for the mirror image of the particle sample to fall on the center axis. As a result, the detector is oriented perpendicular to the center axis for it to perceive the mirror image of the sample on the center axis. This provides a good position of the detector, which can then easily be adjusted correctly in terms of angle and which can also use the same stand as the carrier and the mirror-supporting means.

The sample holders of the carrier conveniently comprises indentations which offer a space for a particle sample. Thus the particles fall into the indentations when positioned under the particles. This results in an easy way of taking up particles in the sample holders.

According to a preferred embodiment, the sample holders of the carrier comprise through holes in the carrier and a lower particle holding disk which prevents the particles from falling through the holes, the holes and the particle holding disk thus offering a space for a particle sample. Also this embodiment results in an easy way of taking up particle samples in the sample holders. Moreover, the sample holders can easily be emptied by an emptying hole being arranged in the particle holding disk. When a full sample holder arrives at the emptying hole, the particle sample falls out of the sample holder by there being no bottom in the sample holder any longer.

According to another embodiment, the device has a means for generating a subatmospheric pressure on the underside of the carrier, the sample holders of the carrier comprising holes to which particle samples are made to adhere by the subatmospheric pressure. This means that a hole cannot possibly take up a plurality of particles at a time, which ensures the feeding of only one particle at a time.

A plurality of places for optical measurement, which each have a detector, are advantageously arranged in the device, and the illumination can be varied between the places for different analyses. This means that the particles can be analyzed in respect of several different properties in the same sorting out of the particles. The advantages of the device having a long time of exposure in spite of a high feeding speed can be used in all recordings of images.

The objects of the invention are also achieved by a method for optical measuring of small particles, such as grains from cereals and like crops, for analysis of the quality of the particles. The method comprises the steps of feeding particle samples which each comprise at least one particle, to a place for optical measurement, following the movement of a particle sample with a mirror in such manner that, in the place for optical measurement, a mirror image of the particle sample falls on a center axis of the movement of the mirror, illuminating the particle sample when located in the place for optical measurement, and recording at least one result of an optical measurement of the illuminated particle sample by means of a detector which is sensitive to electromagnetic radiation. The mirror image of the particle sample stands essentially still seen from the detector, when the measurement is being recorded, owing to the fact that the mirror image of the particle sample falls on the center axis of the movement. The method provides an automatic technique of recording, quickly and with conventional detectors, results of optical measurements for analysis of particles. The particles can be fed at a high speed, without making it too difficult for conventional equipment to satisfy the requirements as to a minimum time of exposure in the detector.

The method preferably comprises the step of analyzing the recorded image by means of image analysis to determine the quality of the particle sample. This means that the analysis can occur directly in the recording of the image, and a sample result can be obtained from the device, quickly and on the spot.

BRIEF DESCRIPTION OF THE DRAWINGS

A presently preferred embodiment of the invention will now be described by way of example with reference to the accompanying drawings.

DETAILED DESCRIPTION OF A PREFERRED EMBODIMENT

Figure 1:
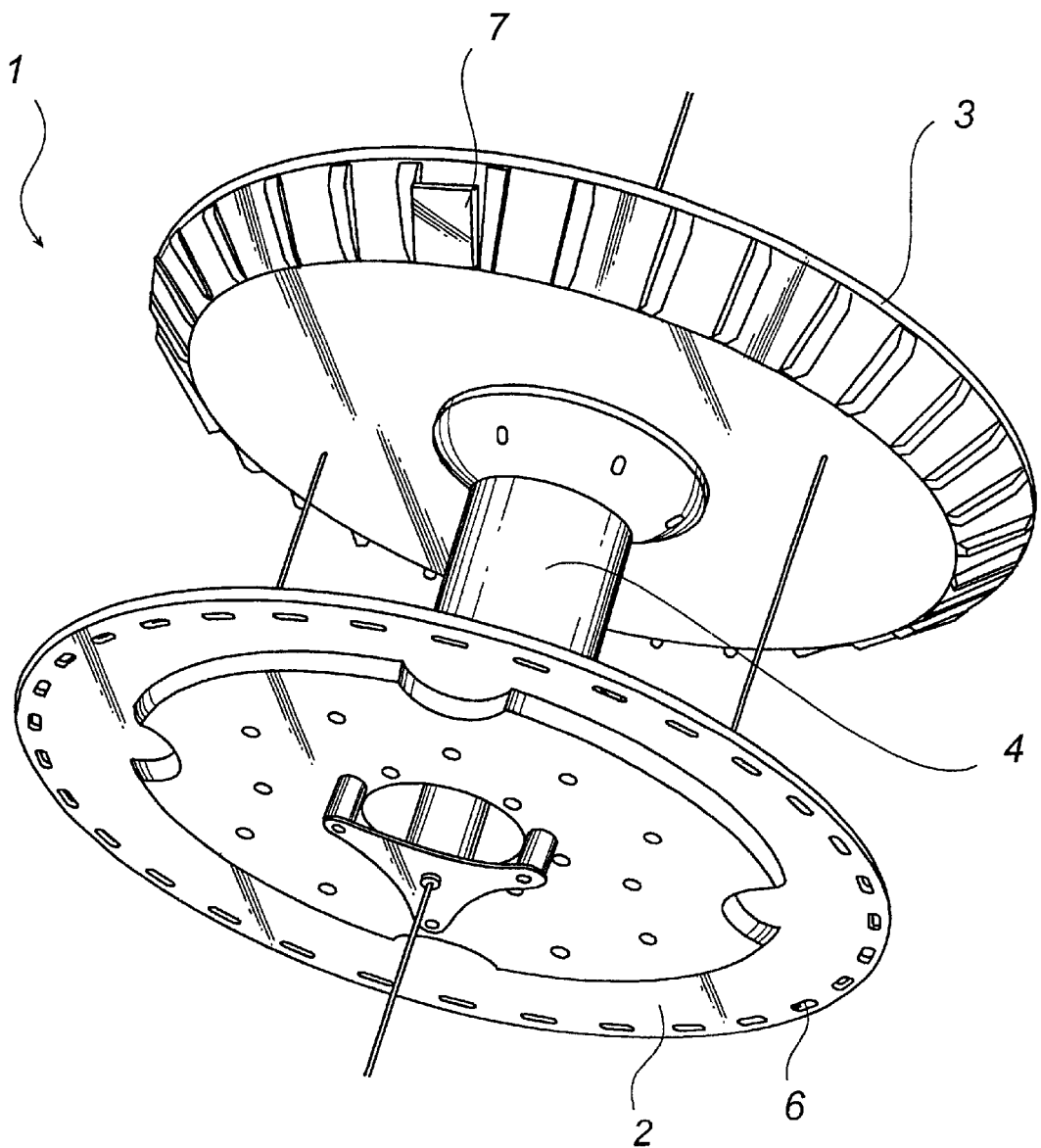
FIG. 1 is a perspective view of a sample-feeding carrier and a mirror-supporting means according to the invention.

FIG. 1 shows a sample-feeding unit 1, which comprises a sample-feeding carrier 2 in the form of a disk and a mirror-supporting means 3. These are interconnected by a central shaft 4, which makes their movements synchronized. The carrier 2 is adapted to feed the particles 5 which are to be analyzed to a place where an image of the particle 5 can be recorded.

Sample holders 6 in the form of holes are arranged along the outer edges of the carrier 2 and adapted to take up particles 5 which are to be analyzed. For each hole 6, there is a matching mirror 7, which is placed on the mirror-supporting means 3 in such manner that a mirror image of a particle 5 in the hole 6 is projected onto a center axis of the mirror-supporting means 3. The mirrors 7 are plane and arranged at an angle of 45° to the center axis, which means that the mirror image of the particle 5 is turned through 90°.

The carrier 2 can be dismounted from the central shaft 4 to be replaced by other carriers 2. This allows adaptation to different kinds of crops by the carrier 2 being exchanged. The sample holders 6 on each carrier 2 are then adapted to a certain kind of crop.

Figure 2:
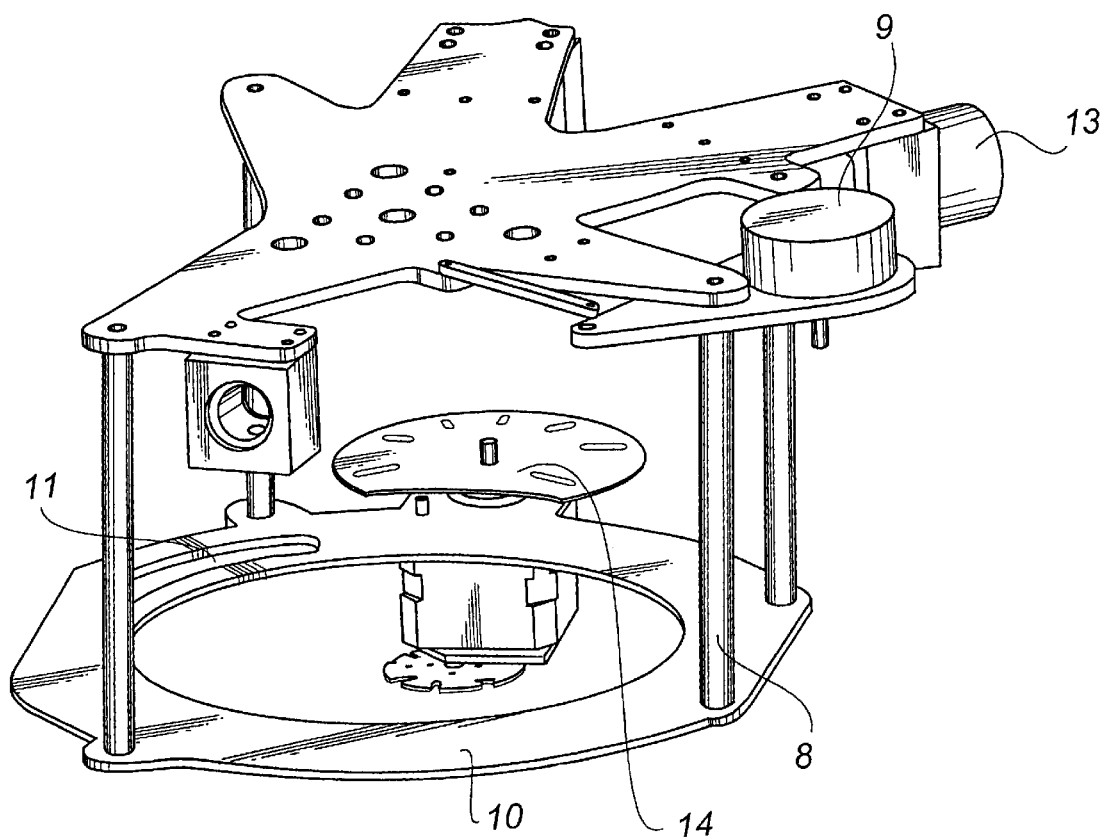
FIG. 2 is a perspective view of a stand in which the carrier and the means in FIG. 1 can be mounted.

The carrier 2 and the mirror-supporting means 3 are circular and rotate in operation about their common shaft 4 for the feeding of samples. The sample-feeding unit 1 is mounted to rotate in a stand 8 which is illustrated in FIG. 2. The rotation is driven by a motor 9 which is mounted on the stand 8.

Particles 5 falling into the holes 6 in the carrier 2 abut against a particle holding disk 10, which prevents the particles 5 from falling through the holes 6. The particle holding disk 10 is therefore arranged immediately below the carrier 2 and thus form a bottom of the holes 6. The holes 6 are formed as the particles 5 and thus control the orientation of the particles 5 in the holes 6. This is applicable to, for example, rice, where, for certain measurements, it is desirable to orient the elongate shape of the grains correctly. This also facilitates the recording of images since the image-recording means can easily be set in such manner that the grains fill the entire surface of exposure.

A particle 5 which is fed by the continuously rotating sample-feeding unit 1 is sliding on the particle holding disk 10 during the entire feeding operation. The particle 5 is fed for optical measurement and is then fed to an emptying hole 11 in the particle holding disk 10. There the particle 5 falls through the emptying hole 11 into a collecting vessel.

The carrier 2 forms an inclined plane, which makes particles 5 that are not taken up in sample holders 6 on the carrier 2, fall down towards a particle holding pocket, at the bottom of the inclined plane. The particle holding pocket forms a wall along part of the circumference of the carrier 2 and prevents the particles 5 from sliding off the carrier 2. A particle 5 abutting against the wall of the particle holding pocket is positioned at the same distance as the sample holders 6 from the center of the carrier 2. All particles in a sample will therefore be taken up by sample holders 6 as they rotate up to the particle holding pocket.

When the particles 5 fall through the emptying hole 11, the sample holder 6 will be empty, and when the carrier 2 is rotated, the sample holder 6 will then arrive at the particle holding pocket where a new particle 5 is taken up. Should two particles 5 fall into the same hole 6, one of them will protrude from the hole 6. The sample holder 6 passes a brush which sweeps the protruding particle 5 away from the hole 6. If a particle 5 is broken, it can be so small that two particles 5 can be taken up in the same hole 6. This problem is solved in the recording of the optical measurement and will be discussed further below.

A device for illumination in the form of illuminating means 12 which constitute light sources for illumination of the particles 5 can be mounted in various ways. They can be mounted adjacent to each sample holder 6 on the carrier 2 in the form of surface-mounted light-emitting diodes or somewhere on the stand 8. The light source can then be mounted, for example, under the carrier 2, in which case transmitted light is measured, or adjacent to a detector 13, in which case reflected light is measured. The illuminating means 12 can, of course, be any kind of light source whatever, such as some sort of laser or a gas discharge lamp.

The detector 13 is mounted on the stand 8 in such manner that an angle between the direction in which the detector 13 takes in light, and the plane of a mirror 7 in the mirror-supporting means 3 is the same as the angle between the plane of the mirror 7 and the center axis. Such a device means that the detector 13 sees a mirror image of the particle 5 which is projected onto the center axis. Since the mirror 7 is inclined at an angle of 45° to the center axis, the detector 13 is arranged in the plane of the mirror-supporting means 3 and angled to record measurements perpendicular to the movement, i.e. at an angle of 45° to the mirror 7.

The detector 13 suitably is an image-recording means. The image-recording means 13 is in turn in this embodiment a conventional CCD camera. The recorded image will then be obtained in electronic form and can, in the camera, be readily converted into a digital format, which is needed for the continued image analysis. Moreover, the image which is recorded in the camera can be divided into a plurality of images. This is needed if the image comprises several particles. This image is then divided into a plurality of images, so that each image comprises one particle only. Subsequently, the continued image analysis can be carried out in respect of each particle separately.

There is also a reference disk 14, which can be put forward over the carrier 2. The reference disk 14 is operated by a stepping motor which puts forward test plates on the reference disk 14 to be recorded in the detector 13. This means that test plates with known properties can be used to calibrate the detector 13.

Figure 3:
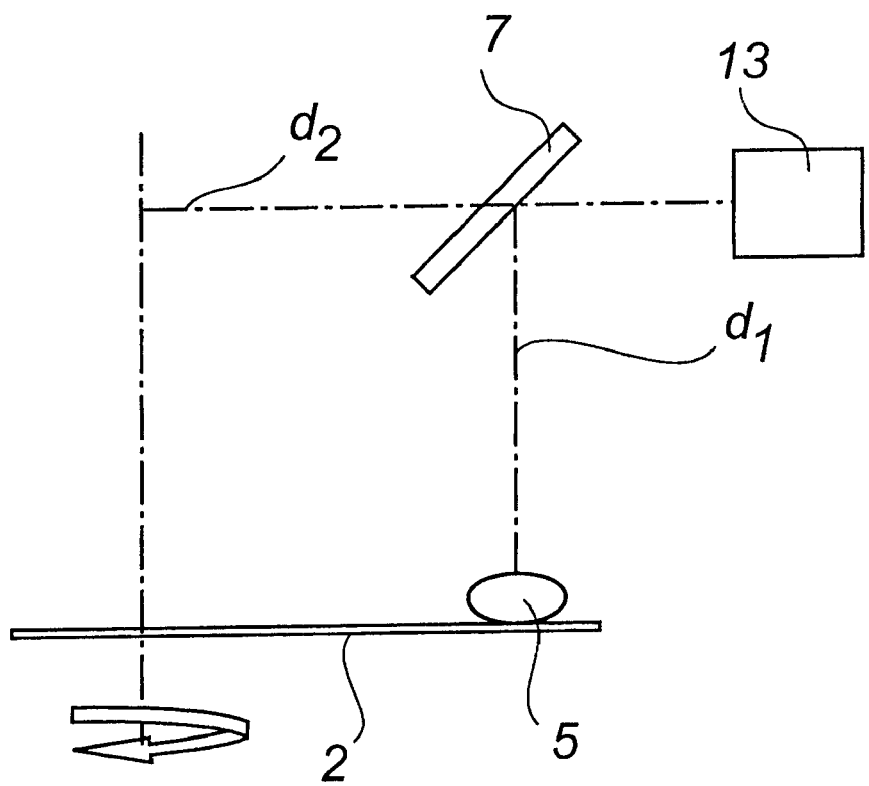
FIG. 3 is a schematic view and illustrates a recording of a mirror image of a particle.

FIG. 3 shows schematically the recording of an image of a particle 5. The particles 5 are fixed in fixed positions on the carrier 2 while the particles are transported past the image-recording means 13. A plane mirror 7 is fixedly arranged above each particle position at an angle of 45° and rotates with the carrier 2. The distance between the center of the particle 5 and the mirror 7 ($d_1$) should be the same as the distance between the mirror 7 and the center axis of the carrier 2 ($d_2$) for the mirror image of the particle 5 to be projected onto the center axis. The distance to the image-recording means 13 is determined by the optics used to obtain the desired properties.

The image-recording means 13, which is fixedly arranged, sees in this way the mirror image projected onto the center axis of the carrier 2 during the time when the mirror 7 is in front of the image-recording means 13. The effect will be a stationary mirror image for a certain time which is dependent on the speed of rotation and size of the carrier 2 and the mirror 7. The mirror image, however, is not quite stationary. The particle 5 is turned round its center, but the angle of this turning is the same as the angle through which the carrier 2 is turned during the time when the mirror 7 is in front of the image-recording means 13. This is such a small angle that the turning of the particle 5 does not cause movement blur in an image that is being recorded by the image-recording means 13.

The extended time which is now available to collect measuring data increases significantly, which radically simplifies the construction for illumination and the other components in the system. Thanks to the extended time, the detector 13 manages to make a plurality of optical measurements of the particle 5 during the time when the particle 5 is in front of the detector.

Also other optical measuring methods that one wants to combine with quick feeding of samples can use the solution described above.

A method of optical measuring of particles 5 for analysis will now be described in more detail. A sample which is to be analyzed is placed in a funnel in the analysis instrument.

In most cases, the sample consists of about 1200 grains or particles (about 30 g), but can be up to 150 g. The sample is then passed down to the particle holding pocket which is mounted at the opening of the funnel. The sample mechanism is started and the particles 5 are separated individually on the carrier 2 and fed to a camera 13. Here the particle 5 is illuminated and the camera 13 records an image of the illuminated particle 5. The carrier 2 is rotated in a continuous movement, but by the arrangement of the mirror-supporting means 3, which has been described above, a relatively long time of exposure can be used in the camera 13 without movement blur arising. Then the particle 5 is fed to further cameras 13, if any, which record images of the particle 5 in different lighting. After all the necessary images of the particles 5 have been recorded, the sample-feeding unit 1 continues to feed the particle, which is then released into the collecting vessel. The recorded images are analyzed to discover defects on the particles 5, such as discolorations, damage etc. When the analysis of the sample is completed, after about 1 min, the result is shown on a display and the operator can empty the collecting vessel. The result shows statistics of the amount of particles having different types of damage and the amount that was approved.

It will be appreciated that a great number of modifications of the above embodiment are feasible within the scope of the invention as defined by the appended claims. For instance, the sample holder of the carrier could be designed in some other manner. The holes could be so small that a particle cannot fall therethrough. The particle holding disk would in that case be replaced by a fan which generates a subatmospheric pressure on the underside of the carrier. The particles would then be fixed by suction to the holes by the subatmospheric pressure, and owing to the holes being small the particles could not fall therethrough. Moreover, two particles could not stay at one hole since the hole is smaller than the particles and the subatmospheric pressure causes the particles to stay with their center over the hole. The particles having passed the optical measurement, the carrier could pass a place where there is no subatmospheric pressure under the carrier. The particles will then fall off from the inclined carrier into a collecting vessel.

The sample holders of the carrier could also be formed as indentations in the carrier. The particles would then fall down into these indentations and in this manner be advanced to the optical measurement. The emptying of the sample holders could then take place by the particles being blown out or being pushed out by means of a brush.

Alternatively, thanks to the possibility of dividing an image of several particles, particle samples comprising a plurality of particles can be fed on the carrier. A plurality of particles will then be measured simultaneously, but the image must be divided into a plurality of images of one particle each.

According to a further alternative embodiment, the mirrors of the mirror-supporting means could be arranged at a different angle to the center axis. The image-recording means would then need to be dislodged accordingly, so that the mirror image of the particle stands still seen from the image-recording means.

The optical measurement can be any kind of light-sensitive measurement. The detector need not record an image but can record the light intensity in certain points or some kind of averaging among a plurality of properties, such as directly reflected light compared with diffusely reflected light. An image-recording means could be, for instance, another type of digital camera, such as a CMOS camera.

Furthermore the sample-feeding unit need not rotate during continuous movement, but this is in most cases advantageous since it causes insignificant wear on mechanical parts.

What we claim and desire to secure by Letters Patent is:

1. A device for optical measuring of small particles, such as grains from cereals and like crops, for analysis of the quality of the particles, which comprises a sample-feeding carrier which is adapted to take up particle samples, which each comprise at least one particle, in sample holders and transport the particle samples to a place for optical measurement, a mirror-supporting means which follows the movement of the carrier and has a mirror for each sample holder, a device for illuminating a particle sample when this is positioned for optical measurement, and a detector which is sensitive to electromagnetic radiation for recording at least one result of an optical measurement of the illuminated particle sample, a mirror in the mirror-supporting means reflecting the particle sample so that a mirror image of the particle sample stands essentially still seen from the detector, when the measurement is being recorded, owing to the fact that the mirror image of the particle sample falls on a center axis of the movement of the mirror-supporting means.

2. The device as claimed in claim 1, wherein the sample-feeding carrier is adapted to feed the particle samples during continuous movement.

3. The device as claimed in claim 1, wherein the detector is an image-recording means which records an image of the particle sample in the optical measurement.

4. The device as claimed in claim 3, further comprising a means for image analysis of the recorded image, an image of a particle sample, which comprises a plurality of particles, being, with the aid of the means for image analysis, divisible into images of one particle each.

5. The device as claimed in claim 3, wherein the image-recording means is a digital camera.

6. The device as claimed in claim 1, wherein the sample holders are adapted to take up only one particle.

7. The device as claimed in claim 1, wherein the carrier is circular and rotates to feed the particle samples.

8. The device as claimed in claim 7, wherein the mirror-supporting means and the carrier are interconnected by a center shaft and thus follow each other's movements.

9. The device as claimed in claim 1, wherein the mirrors in the mirror-supporting means are arranged at an angle of 45° to the center axis, the distance between the particle sample and the associated mirror being the same as the distance between the mirror and the center axis for the mirror image of the particle sample to fall on the center axis.

10. The device as claimed in claim 1, wherein the sample holders of the carrier comprise indentations which offer a space for a particle sample.

11. The device as claimed in claim 1, wherein the sample holders of the carrier comprise through holes in the carrier and a lower particle holding disk which prevents the particles from falling through the holes, the holes and the particle holding disk thus offering a space for a particle sample.

12. The device as claimed in claim 1, further comprising a means for generating a subatmospheric pressure on the underside of the carrier, the sample holders of the carrier comprising holes to which particle samples adhere by means of the subatmospheric pressure.

13. The device as claimed in claim 1, wherein a plurality of places for optical measurement are arranged, which each have a detector, the illumination being variable between the places for different analyses.

14. A method for optical measuring of small particles, such as grains from cereals and like crops, for analysis of the quality of the particles, comprising the steps of feeding particle samples which each comprise at least one particle, to a place for optical measurement, following the movement of a particle sample with a mirror in such manner that, in the place for optical measurement, a mirror image of the particle sample falls on a center axis of the movement of the mirror, illuminating the particle sample when positioned for optical measurement, and recording at least one result of an optical measurement of the illuminated particle sample by means of a detector which is sensitive to electromagnetic radiation, the mirror image of the particle sample standing essentially still seen from the detector, when the measurement is being recorded, owing to the fact that the mirror image of the particle sample falls on the center axis of the movement.

15. The method as claimed in claim 14, wherein the particle samples are fed during continuous movement.

16. The method as claimed in claim 14, wherein the detector is an image-recording means which records an image of the particle sample in the optical measurement.

17. The method as claimed in claim 16, further comprising the step of dividing an image of a particle sample which comprises a plurality of particles, into images of one particle each.

18. The method as claimed in claim 16, further comprising the step of analyzing the recorded image by image analysis for determining the quality of the particle sample.

19. The method as claimed in claim 16, wherein a digital camera is used as the image-recording means.

20. The method as claimed in claim 14, wherein only one particle is fed in each particle sample.

21. The method as claimed in claim 14, wherein the particle samples are fed by sample holders in a circular carrier, which is rotated to feed the particle samples.

22. The method as claimed in claim 21, wherein a mirror-supporting means, which supports mirrors, which follow particle samples, is connected to the carrier via a center shaft and thus made to follow the movements of the carrier and the particle samples.

23. The method as claimed in claim 22, wherein the mirrors of the mirror-supporting means are arranged at an angle of 45° to the center axis, the distance between a particle sample and the associated mirror being the same as the distance between the mirror and the center axis for the mirror image of the particle sample to fall on the center axis.

24. The method as claimed in claim 21, wherein the sample holders of the carrier comprise indentations which offer a space for a particle sample.

25. The method as claimed in claim 21, wherein the sample holders of the carrier comprise through holes in the carrier and a lower particle holding disk which prevents the particles from falling through the holes, the holes and the particle holding disk thus offering a space for a particle sample.

26. The method as claimed in claim 21, wherein a means for generating a subatmospheric pressure is arranged on the underside of the carrier, the sample holders of the carrier comprising holes to which particle samples are made to adhere by the subatmospheric pressure.

27. The method as claimed in claim 14, further comprising the step of recording a plurality of optical measurements of each particle sample with different kinds of illumination during the measurements, the recordings occurring in different places by means of a plurality of detectors.

* * * * *

UNITED STATES PATENT AND TRADEMARK OFFICE
CERTIFICATE OF CORRECTION

PATENT NO. : 6,556,295 B2
DATED : April 29, 2003
INVENTOR(S) : Erland Leide et al.

It is certified that error appears in the above-identified patent and that said Letters Patent is hereby corrected as shown below:

<u>Title page,</u>
Item [75], Inventor, after "Ylikangas, Rydeback (SE)" insert the following:
-- Peter Hansson, Stockholm (SE) --.

Signed and Sealed this

Thirtieth Day of September, 2003

JAMES E. ROGAN
*Director of the United States Patent and Trademark Office*